(12) United States Patent
Dabney et al.

(10) Patent No.: US 10,293,148 B2
(45) Date of Patent: May 21, 2019

(54) **SYSTEM, RETAINER AND METHOD OF PREVENTING AND TREATING NOSOCOMIAL INFECTIONS INCLUDING METHICILLIN-RESISTANT *STAPHYLOCOCCUS AUREUS* INFECTIONS**

(71) Applicants: Paul Dabney, Georgetown, TX (US); Harry Jung, III, Georgetown, TX (US); James Elliott, Arlington, TX (US)

(72) Inventors: Paul Dabney, Georgetown, TX (US); Harry Jung, III, Georgetown, TX (US); James Elliott, Arlington, TX (US)

(*) Notice: Subject to any disclaimer, the term of this patent is extended or adjusted under 35 U.S.C. 154(b) by 115 days.

(21) Appl. No.: 15/399,955

(22) Filed: Jan. 6, 2017

(65) Prior Publication Data
US 2018/0193622 A1    Jul. 12, 2018

(51) Int. Cl.
*A61M 37/00*    (2006.01)
*A61K 31/7056*    (2006.01)
(Continued)

(52) U.S. Cl.
CPC ............ *A61M 37/00* (2013.01); *A61F 7/007* (2013.01); *A61K 31/7048* (2013.01);
(Continued)

(58) Field of Classification Search
CPC ....... A61C 19/06; A61M 37/00; A61M 11/00; A61M 25/0082; A61F 7/007;
(Continued)

(56) References Cited

U.S. PATENT DOCUMENTS

| 4,906,670 A | * | 3/1990 | Higashi | A61K 9/0063 |
|---|---|---|---|---|
| | | | | 514/773 |
| 5,188,817 A | * | 2/1993 | Ozick | A61K 8/671 |
| | | | | 424/435 |

(Continued)

FOREIGN PATENT DOCUMENTS

WO    2011/008441 A1    1/2011

OTHER PUBLICATIONS

Notification of Transmittal of the International Search Report and the Written Opinion of the International Searching Authority dated May 21, 2018, in connection with corresponding International Application No. PCT/US2018/012130 (15 pgs.).

*Primary Examiner* — Nicholas D Lucchesi
(74) *Attorney, Agent, or Firm* — Maier & Maier, PLLC

(57) ABSTRACT

According to an exemplary embodiment, a retainer for therapeutic treatment may be provided. The retainer for therapeutic treatment may include: a retainer that may retain a antimicrobial solution against tissue; a number of heating elements connected to the retainer for therapeutic treatment; a number of power supply cables connected to the number of heating elements; a number of antimicrobial solution delivery elements connected to the retainer for therapeutic treatment that may deliver an antimicrobial solution; a number of pieces of tubing having a first end connected to a antimicrobial solution reservoir and a second end connected to a number of antimicrobial solution delivery elements; a number of fiber optic cables having a first end connected to a light source; and a number of light terminations rigidly connected to the retainer for therapeutic treatment and connected to the second end of the fiber optic cable.

19 Claims, 7 Drawing Sheets

(51) Int. Cl.
*A61K 31/7048* (2006.01)
*A61F 7/00* (2006.01)
*A61M 35/00* (2006.01)
*A61M 25/00* (2006.01)
*A61N 5/06* (2006.01)
*A61N 5/067* (2006.01)
*A61C 13/15* (2006.01)
*A61C 19/06* (2006.01)

(52) U.S. Cl.
CPC ..... *A61K 31/7056* (2013.01); *A61M 25/0082* (2013.01); *A61M 35/00* (2013.01); *A61N 5/0624* (2013.01); *A61C 19/004* (2013.01); *A61C 19/063* (2013.01); *A61F 2007/0017* (2013.01); *A61F 2007/0037* (2013.01); *A61F 2007/0059* (2013.01); *A61F 2007/0062* (2013.01); *A61M 2037/0007* (2013.01); *A61N 2005/063* (2013.01); *A61N 2005/067* (2013.01); *A61N 2005/0636* (2013.01); *A61N 2005/0645* (2013.01); *A61N 2005/0652* (2013.01); *A61N 2005/0663* (2013.01)

(58) Field of Classification Search
CPC ............ A61K 31/7048; A61K 31/7056; A61N 5/0601; A61N 5/0602
See application file for complete search history.

(56) References Cited

U.S. PATENT DOCUMENTS

| | | | | |
|---|---|---|---|---|
| 5,275,804 | A * | 1/1994 | Michaels | A61K 8/40 424/49 |
| 6,056,548 | A * | 5/2000 | Neuberger | A46B 15/0002 433/215 |
| 6,893,259 | B1 | 5/2005 | Reizenson | |
| 7,118,377 | B2 * | 10/2006 | Inoue | A61C 17/0211 433/80 |
| 8,915,948 | B2 * | 12/2014 | Altshuler | A61B 5/6843 128/898 |
| 9,636,195 | B2 * | 5/2017 | Wolpo | A61C 17/3481 |
| 9,700,735 | B2 * | 7/2017 | Dabney | A61N 5/062 |
| 9,884,203 | B2 * | 2/2018 | Dabney | A61N 5/062 |
| 9,931,189 | B2 * | 4/2018 | Dabney | A61D 7/00 |
| 2003/0198605 | A1 * | 10/2003 | Montgomery | A61C 5/00 424/53 |
| 2005/0026103 | A1 * | 2/2005 | Wasylucha | A61C 3/005 433/29 |
| 2005/0089819 | A1 * | 4/2005 | Allred | A61C 5/00 433/215 |
| 2006/0240375 | A1 * | 10/2006 | Soukos | A61C 19/06 433/29 |
| 2007/0238660 | A1 * | 10/2007 | Michielsen | A01N 43/42 514/290 |
| 2008/0255498 | A1 * | 10/2008 | Houle | A61C 17/02 604/20 |
| 2009/0136893 | A1 * | 5/2009 | Zegarelli | A61C 19/063 433/80 |
| 2009/0208543 | A1 * | 8/2009 | Nathoo | A61K 8/02 424/401 |
| 2011/0123958 | A1 * | 5/2011 | Piergallini | A61C 19/063 433/217.1 |
| 2012/0052461 | A1 * | 3/2012 | Hayes | A61C 19/066 433/29 |
| 2013/0006119 | A1 | 1/2013 | Pan et al. | |
| 2014/0315142 | A1 * | 10/2014 | Montgomery | A61C 19/066 433/29 |
| 2016/0015494 | A1 * | 1/2016 | Dabney | A61C 19/063 433/29 |
| 2016/0015498 | A1 * | 1/2016 | Dabney | A61D 7/00 604/20 |
| 2016/0015744 | A1 * | 1/2016 | Dabney | A61K 33/40 424/616 |
| 2016/0015745 | A1 * | 1/2016 | Dabney | A61K 33/40 424/85.1 |
| 2016/0015909 | A1 * | 1/2016 | Dabney | A61C 19/063 604/20 |
| 2016/0015998 | A1 | 1/2016 | Dabney | |
| 2016/0015999 | A1 * | 1/2016 | Dabney | A61N 5/062 433/29 |
| 2016/0354407 | A1 | 12/2016 | Dabney | |
| 2017/0120071 | A1 * | 5/2017 | Dabney | A61K 8/22 |
| 2017/0173352 | A1 * | 6/2017 | Dabney | A61N 5/062 |

* cited by examiner

SYSTEM, RETAINER AND METHOD OF PREVENTING AND TREATING NOSOCOMIAL INFECTIONS INCLUDING METHICILLIN-RESISTANT *STAPHYLOCOCCUS AUREUS* INFECTIONS

BACKGROUND

A hospital acquired infection (HAI), also known as nosocomial infection, is an infection that is acquired or contracted from a hospital or other medical care facility. The hospital environment can consist of an inpatient or outpatient hospital or surgical center, nursing home, rehabilitation facility, clinic, home healthcare environment or other area of patient care. HAIs may be endogenous, arising from an infectious agent present within a patient's body, or exogenous, transmitted from another source within the hospital or medical care facility. In the United States, the Centers for Disease Control and Prevention (CDC) estimates that nosocomial infections contribute to roughly 100,000 deaths each year from an estimated 1,750,000 HAIs. In addition to patient-to-patient spread, disease transmission may involve medical care staff, personnel, students, visitors, voluntary workers, and the like.

According to the CDC, the most common bacteria associated with nosocomial infections is *Staphylococcus aureus*. *Staphylococcus aureus* mutates into an antibiotic resistant strain (MRSA) that is difficult to treat and even regularly mutates into a strain that does not respond to treatment resulting in patient death. The CDC estimates 72,444 patients had invasive MRSA infections in 2014 and 9,194 of those infected patients died as a result. MRSA infection rates may be underestimated because of limited or inaccurate surveillance. MRSA infections now contribute to more deaths than does HIV and its threat level is rising. Various treatments and preventative measures have been trialed; however, there is a concern that use of antibiotic modalities could lead to greater resistance.

Nosocomial infections by *Staphylococcus epidermidis* ("*S. epidermidis*"), a less virulent cousin of *Staphylococcus aureus*, have also gained significant attention due to the ubiquity of the bacterium as a human commensal microorganism. Specifically, *S. epidermidis* is the most frequently isolated species from human epithelia. While previously regarded as an innocuous skin colonizer, *S. epidermidis* now represents the most common source of infections on indwelling medical devices. The high rate of infection most likely stems from the fact that *S. epidermidis* is a permanent part of the human epithelial microflora, resulting in high probability of device contamination during insertion. Although rarely life-threatening, nosocomial infections by *S. epidermidis* represent a serious burden for the public health system due to their frequency and difficulty of treatment. In the United States alone, an estimated $2 billion is spent annually on costs related to vascular catheter-related bloodstream infections caused by *S. epidermidis*. Treatment is complicated by specific antibiotic resistance genes and the formation of biofilms, multicellular accumulations that have intrinsic resistance to antibiotics and mechanisms of host defense.

Moreover, nosocomial infections by herpes simplex virus type 1 ("HSV-1"), although relatively infrequent, have also been reported by the medical community. HSV-1 is an enveloped, double-stranded DNA virus commonly known as a "cold sore." HSV-1 is usually acquired through direct contact with infected lesions, sores, and/or oral secretions, such as through kissing or sharing drinking glasses with an infected individual. While infection is mostly asymptomatic, symptoms of the virus include painful blisters or open sores in the skin or mucous membranes of the mouth, lips or genitals. Currently, there is no cure for HSV-1; it persists in the body by becoming latent and concealing itself in the cell bodies of neurons. Some carriers of the virus will continue to experience episodes of viral reactivation or outbreaks, where virus replication and shedding occurs and causes new sores to appear on the skin. HSV-1 is common worldwide, and it is estimated that the majority of United States citizens are exposed to or infected by HSV-1 by the time they reach adolescence.

Current methods of preventing nosocomial infectious outbreaks in a health care environment include continued education for staff, strict adherence to infection control protocols, and early detection and communication of nosocomial infection events. Nevertheless, the current methods have several limitations in their ability to provide immediate protection to patients and medical staff alike. The treatment modality, described herein, provides a means to successfully eliminate bacteria that causes nosocomial infections preoperatively and postoperatively. The treatment can eliminate the target bacteria before an infection has occurred and also eliminate the bacteria causing an ongoing infection.

SUMMARY

According to an exemplary embodiment, a retainer for therapeutic treatment may be provided. The retainer for therapeutic treatment may include: a retainer that may retain a antimicrobial solution against tissue; a number of heating elements connected to the retainer for therapeutic treatment; a number of power supply cables connected to the number of heating elements; a number of antimicrobial solution delivery elements connected to the retainer for therapeutic treatment that may deliver an antimicrobial solution; a number of tubes having a first end connected to a antimicrobial solution reservoir and a second end connected to a number of antimicrobial solution delivery elements; a number of fiber optic cables having a first end connected to a light source; and a number of light terminations rigidly connected to the retainer for therapeutic treatment and connected to the second end of the fiber optic cable.

According to another exemplary embodiment, a method of providing therapeutic treatment may be provided. The method of providing therapeutic treatment may include coupling a retainer that may retain an antimicrobial solution against tissue; connecting a number of heating elements connected to the retainer for therapeutic treatment; powering the heating elements; connecting a number of antimicrobial solution delivery elements connected to the retainer for therapeutic treatment; connecting a number of pieces of tubing having a first end connected to an antimicrobial solution reservoir and a second end connected to the number of antimicrobial solution elements; providing a number of fiber optic cables having a first end connected to a light source; connecting a number of light terminations rigidly connected to the retainer for therapeutic treatment and connected to the second end of the fiber optic cable; applying the antimicrobial solution on a tissue to be treated; retaining the antimicrobial solution against the tissue to be treated; providing the selected wavelength of light; bringing the antimicrobial solution to a desired temperature; and irradiating the antimicrobial solution.

BRIEF DESCRIPTION OF THE DRAWINGS

Advantages of exemplary embodiments of the system, retainer and method of providing therapeutic treatment will be apparent from the following detailed description of the exemplary embodiments. The following detailed description should be considered in conjunction with the accompanying figures in which.

DETAILED DESCRIPTION

Aspects of the present invention are disclosed in the following description and related figures directed to specific exemplary embodiments of the invention. Those skilled in the art will recognize that alternate exemplary embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The exemplary embodiments described herein are not limiting, but rather are exemplary only. It should be understood that the described exemplary embodiments are not necessarily to be construed as preferred or advantageous over other exemplary embodiments. Moreover, the terms "exemplary embodiments of the invention", "exemplary embodiments" or "invention" do not require that all exemplary embodiments of the invention include the discussed feature, advantage or mode of operation.

In an exemplary embodiment, and generally referring to the Figures, a system, retainer and method of providing therapeutic treatment may provide a retainer to hold solutions in contact with tissues while the tissues and solutions may be simultaneously exposed to certain wavelengths of light. The antimicrobial solutions may be activated with certain wavelengths of lights and may eliminate or reduce microbes at a higher percentage than the solution alone. An exemplary embodiment of this retainer may create a synergistic effect between certain wavelengths of light and antimicrobial solutions that when applied to tissues may eliminate or reduce disease caused by microorganisms. An exemplary embodiment of this retainer may consist of a retainer for therapeutic treatment that emits certain wavelengths of light into the solution. When a specific light and solution combination is applied to tissues, a synergistic effect may be created that may reduce, and may eliminate microorganisms that cause disease.

Figure 1:
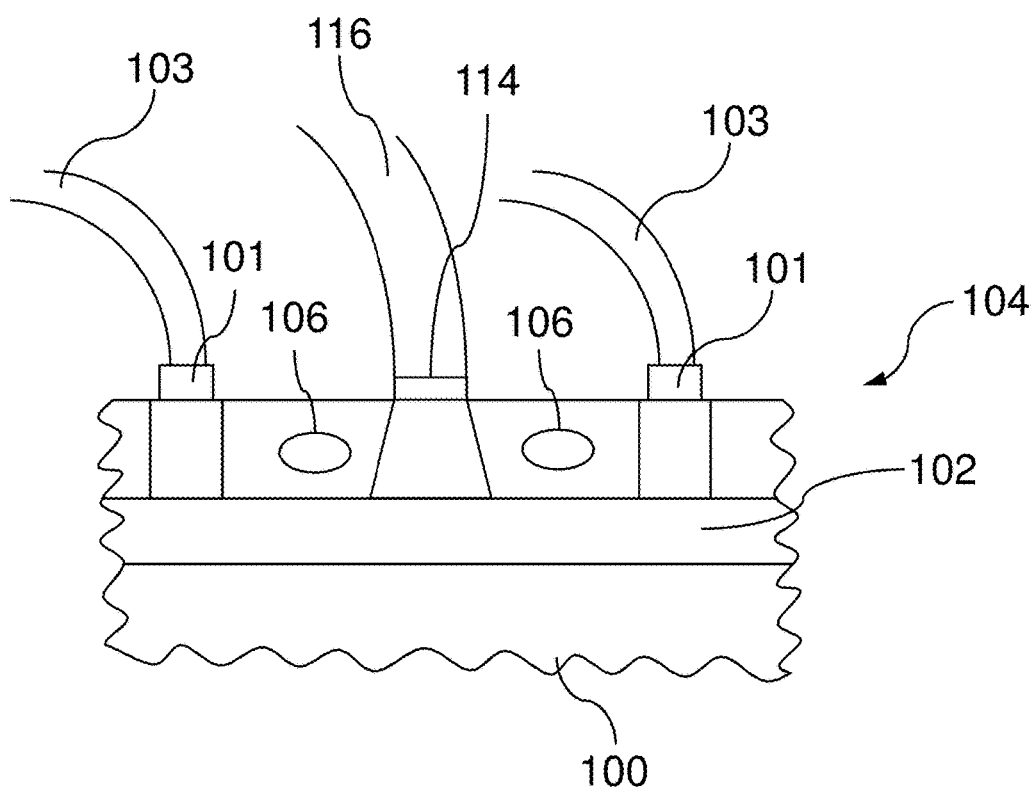
FIG. 1 is a diagram showing an exemplary embodiment of a system, retainer and method of providing therapeutic treatment.

In an exemplary embodiment illustrated in FIG. 1, a layer of antimicrobial solution 102 may be held between the tissue 100 and the retainer for therapeutic treatment 104. In an exemplary embodiment, one end of a number of fiber optic cables 103 may be rigidly attached to the retainer for therapeutic treatment 104 through a number of fiber optic connection interfaces or plugs 101. In a further exemplary embodiment, the second end of the number of fiber optic cables may be rigidly connected to any desired source including, but not limited to, a light emitting diode (LED) and laser. The activation of the antimicrobial solution by a light of a pre-determined wavelength may create a synergistic antimicrobial effect. The resulting synergistic effect may be greater than the effect of an antimicrobial solution or the light acting alone. In an exemplary embodiment, the retainer 104 may include temperature control elements 106 that warm and further activate the antimicrobial solution layer 102. It may be further appreciated that the temperature control elements 106 may also cool the antimicrobial solution, or otherwise regulate the temperature of the antimicrobial solution, as desired. In a further exemplary embodiment, a number of antimicrobial solution delivery elements 114 may be rigidly connected to the retainer 104 for therapeutic treatment 104 and to a number of tubes 116.

In an exemplary embodiment, the retainer for therapeutic treatment 104 may hold solutions in contact with tissues 100, such as flesh or teeth, while the tissues 100 and solutions 102 may be simultaneously exposed to certain wavelengths of light. The retainer for therapeutic treatment 104 may include at least one tooth covering tray that may emit light for oral treatments creating a synergistic antimicrobial effect between an antimicrobial solution and a light of certain predetermined wavelengths. The resulting synergistic effect may be greater than the effect of an antimicrobial solution or the light acting alone. The retainer 104 may be installed on an arch of one or more human teeth. A light source may shine from a light emitting device or from the end of a fiber optic cable. The fiber optic cable may have one side exposed down its length. An antimicrobial solution 102 may fill a dental arch-shaped tray. In an exemplary embodiment, the light source may be blue, or another certain predetermined wavelength of light that may supercharge the solution, with an exposure from, but not limited to, a few second to several minutes, as desired. It may be appreciated that any desired wavelength or exposure time may be applied.

In an exemplary embodiment, an antimicrobial solution 102 may be used without a reservoir. The antimicrobial solution 102 may be inserted directly into the body cavity and exposed to light by a fiber optic wand with a number of light emitting fibers. Further exemplary embodiments of a carrier or reservoir may be the solution 102 itself or a gel. This gel may be inserted in a body cavity with a catheter and exposed to the synergizing light by the same catheter or a different catheter. The synergizing light may create an antimicrobial effect between an antimicrobial solution and a light of certain predetermined wavelengths. The resulting antimicrobial effect may be greater than the effect of an antimicrobial solution or the light acting alone. It may be appreciated that the antimicrobial solution 102 may be delivered by any desired expedient, including, but not limited to, reservoirs, bandages, gels, solutions, head coverings, wraps, socks, stockings, hats, helmets, mitts, suits, tents, probes, and catheters. In another exemplary embodiment, the retainer for therapeutic treatment may be a light emitting sponge that can apply and hold the solution on the surface of the tissue.

Figure 2:
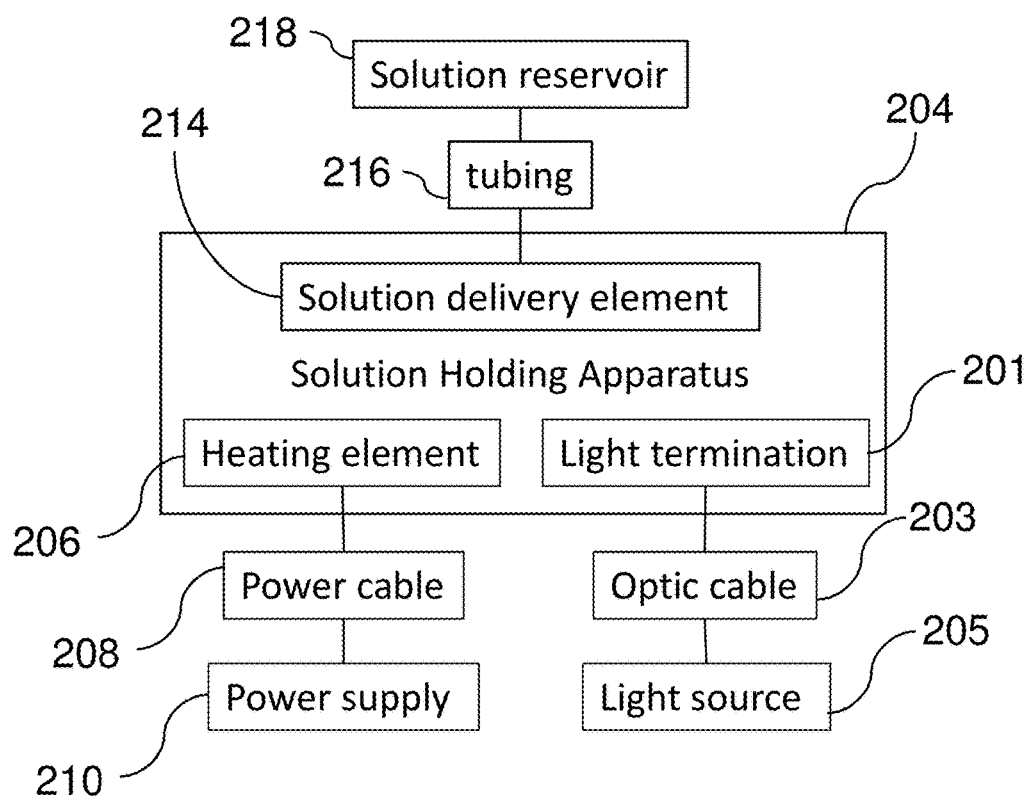
FIG. 2 is a diagram showing another exemplary embodiment of a system, retainer and method of providing therapeutic treatment.

Now referring to exemplary FIG. 2, an exemplary embodiment of a retainer for providing therapeutic treatment may be provided. A retainer for therapeutic treatment 204 may house a number of heating elements 206 connected to a power supply 210 by a power cable 208. In another exemplary embodiment, a retainer for therapeutic treatment 204 may house a number of light terminations 201 that may be connected to a light source 205 by optic cable 203. In a further exemplary embodiment, a retainer for therapeutic treatment 204 may house an antimicrobial solution delivery element 214 connected to an antimicrobial solution reservoir 218 through a tubing 216.

Figure 3:
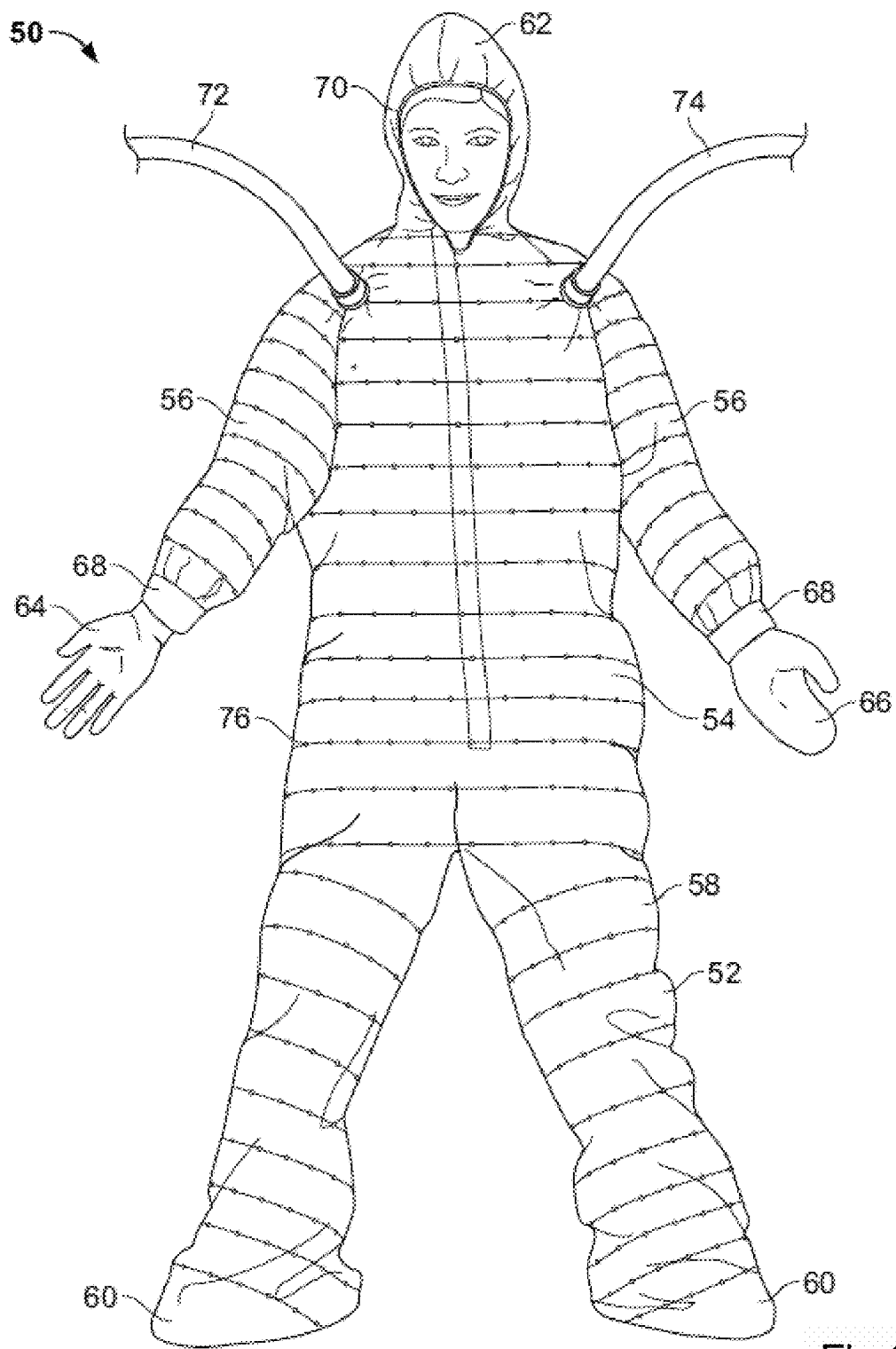
FIG. 3 is a diagram showing an exemplary embodiment of a full body suit retainer.

According to another exemplary embodiment, and generally referring to FIG. 3, a full body suit retainer may be provided. A full body suit with tubing may carry a light-enhanced antimicrobial mist or solution to a user wearing the suit. An embodiment of a suit may include a one-piece garment that generally retains air around the user's body. Exemplary embodiments of a full body suit may include a portion that covers at least a user's torso, as desired. Exemplary embodiments may further include portions to cover a user's legs, feet, arms, head, or hands, as desired. Further exemplary embodiments may have collars, cuffs, or elastic portions that may fit against the user to help retain the antimicrobial solution, as desired. The portions may cooperate to provide a garment that may retain the antimicrobial solution within the suit when the suit is worn. A fiber optic cable may wrap around the inside of the suit. A full body suit may include sleeves with gloves or mittens, pants with feet, and a hood with fiber optic cable spaced along the inner fabric of the suit, or otherwise within or on the fabric.

In an exemplary embodiment, gloves, mittens, or feet may help retain the antimicrobial solution within the suit, and may be integrated with the rest of the suit or may be removable. Exemplary embodiments of integrated portions may include fiber optic cable, similar to the rest of the suit. Exemplary embodiments of removable portions may lack fiber optic cable, or may include fiber optic cable that can be connected to the fiber optic cable in the sleeves or pants, as desired. The fiber optic cable may have light terminations spaced along the fiber optic cable inside the suit. The fiber optics may irradiate an antimicrobial solution with a light of certain predetermined wavelengths and may create a synergistic antimicrobial effect. The resulting synergistic effect may be greater than the effect of an antimicrobial solution or the light acting alone. An exemplary embodiment may include a heating element inside the body suit, such heating wires may be embedded in the fabric of the suit.

In a further exemplary embodiment, the suit may include an input tube or input tubing to carry antimicrobial solution into the suit, an area within the suit to circulate the antimicrobial solution against the user, and an exhaust tube or exhaust tubing to allow air and the antimicrobial solution out of the suit. Exemplary embodiments of tubing may include an input tube on one side of the torso and an output tube on the opposite side, such as input and output tubes on opposite shoulders.

In an exemplary embodiment, a user may put on the garment, add anti-microbial solution using the input tube, allow the mist to circulate within the suit, and turn on the light source. The user may simultaneously input and output antimicrobial solution to circulate through the suit. The user may power on the heating element to warm the mist and/or otherwise activate or control any portion of the suit, as desired.

Further to the above, another exemplary embodiment of the therapeutic treatment retainer may be illustrated in FIG. 3. An embodiment of a medical device 50 may include a full body suit 52 having an integrated torso portion 54, sleeves 56, pants 58, feet 60, and a hood 62, and removable gloves 64 or mittens 66. The sleeves 56 may have cuffs 68 to tighten and/or form a seal against the user's wrists. The hood 62 may have elastic portions 70 to tighten against the user's face. Further exemplary embodiments may include an input tube 72, such as one located on shoulder of the torso portion 54, and an exhaust tube 74 on the opposite shoulder of the torso portion 54. Exemplary embodiments may further include a fiber optic cable 76 spaced along the inner fabric of the suit 52. Fiber optic cable 76 may be coupled to the suit 52 in any desired fashion.

Figure 4:
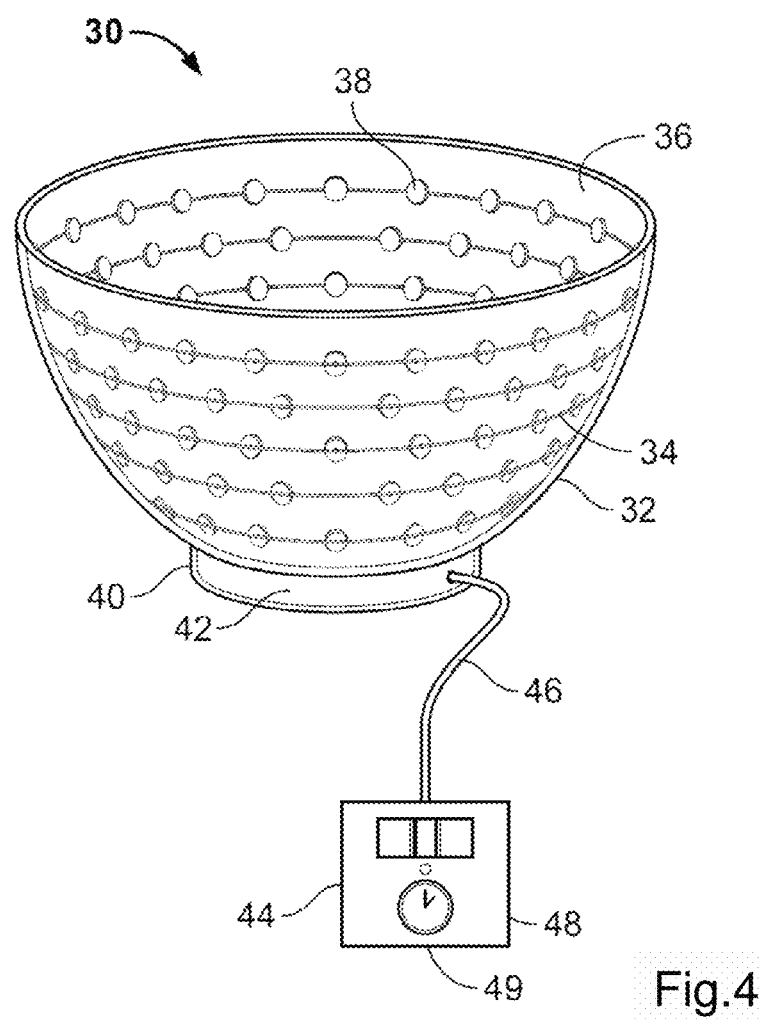
FIG. 4 is a diagram showing an exemplary embodiment of a bowl retainer.

In further exemplary embodiment, and generally referring to FIG. 4, the retainer may be in the shape of a container and may apply an antimicrobial solution that may be enhanced with light of a predetermined wavelength. An exemplary embodiment may include a bowl, such as a round, open-top container that retains an antimicrobial solution. The bowl may be made of generally watertight material so it can retain liquid solution. A fiber optic cable may wrap all around the inside surface of the bowl, with light terminations spaced along the fiber optic cable. The fiber optic cable may have a number of light terminations so that an antimicrobial solution in the bowl is lighted with light from the cable so as to substantially surround an item immersed in the bowl. An exemplary embodiment may include a heating element at the bottom of the bowl. The bowl may have a stand or base, and the heating element may be located in the base, or any other location, as desired. The fiber optic cable may connect through a connection cable to a light source. The light source may have an on/off switch and may have a timer control. Embodiments may include a control box that includes the light and heating power source, such as batteries or a connection to a power outlet. Embodiments of a control box may also include controls for turning the light or heater on or off, setting of timers, and status display. A control box may include receptacles or cables for interfacing with the rest of the retainer, such as a combined interface for both fiber optics and heater power.

In an exemplary embodiment, the antimicrobial solution may be warmed in the bowl. An object or a body part such as fingers may be placed into the antimicrobial solution, and the light source may be turned on. The light source may interact with the antimicrobial solution and may create a synergistic antimicrobial effect. The resulting synergistic effect may be greater than the effect of an antimicrobial solution or the light acting alone. The user may utilize a control box, or any other wired or wireless controller, to turn on or off, or set timers for, the light source, the heater power, or both. It may be appreciated that any desired functions may be managed and timed by the control box.

As depicted in exemplary FIG. 4, an embodiment of a medical device 30 may include a bowl 32 with a number of fiber optic cables 34 that may wrap around an inside surface 36 of the bowl 32. The number of fiber optic cable 34 may have any number of light terminations 38. Exemplary embodiments may have a base 40, which may contain a number of heating elements 42. The fiber optic cable 34 may connect to a number of light sources 44 through a number of fiber optic connection cables 46. The number of light sources 44 may include an off/off switch 48 or a timer control 49.

Figure 5:
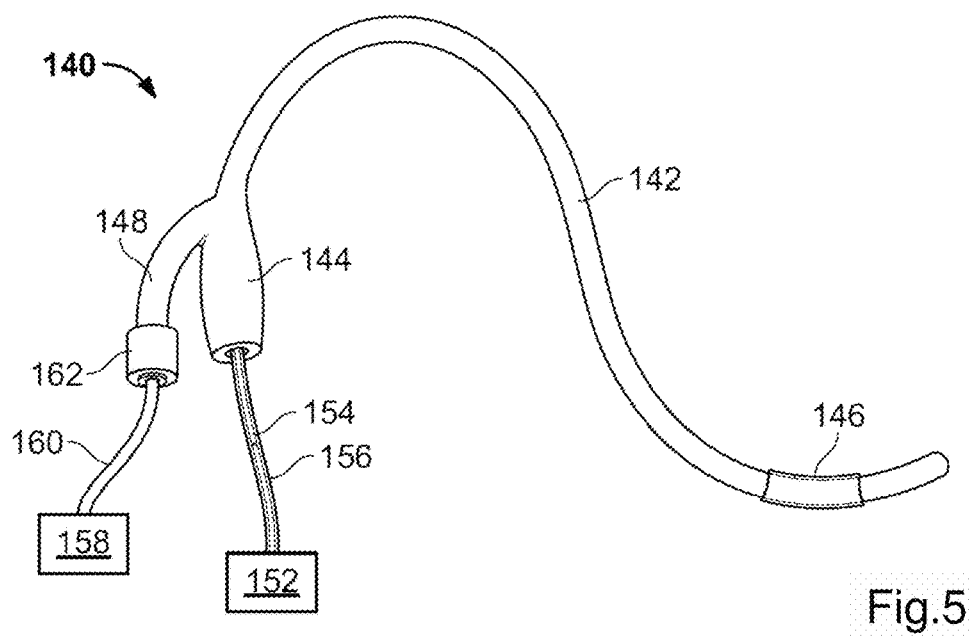
FIG. 5 is a diagram showing an exemplary embodiment of a catheter retainer.

In an exemplary embodiment, and referring generally to FIG. 5, the retainer may include a catheter that can be inserted into a user's body to dispense antimicrobial fluid. Embodiments may also dispense other medicines or fluids, or may be used in a surgical procedure, as desired. An exemplary embodiment of a catheter may include a light source running into a fiber optic cable, a catheter tube, a mesh to dispense antimicrobial solution, and a termination emitting light. The antimicrobial solution may pass into a first end of the catheter tube, which may be a thin tube or canal down the center of the catheter, made of medical grade materials. An exemplary embodiment may receive medicine or antimicrobial solution in one end of the tube, which may be dispensed out of a mesh near an opposite or distal end of the tube.

Additional exemplary embodiments may include an integrated heating element to warm the antimicrobial solution while in use, or a separate heater to warm the antimicrobial solution before use. An exemplary embodiment may also include a thin fiber optic cable inside the catheter tube, or the catheter tube itself may be made of fiber optic material so that the tube conducts both light and antimicrobial solution. A number of light terminations may be positioned at, or proximate, an end of the tube, near the mesh portion so that the light shines onto the antimicrobial solution when the solution may be dispensed into the user. An exemplary embodiment may include a light emitting cable that may be integrated with the catheter, or a light emitting cable that may be separated from the catheter tube carrying the antimicrobial solution.

In a further exemplary embodiment, the catheter may be inserted into a body cavity, and may be used for purposes such as drainage or administration of therapeutic materials before or after the device may be used to apply antimicrobial solution. Antimicrobial solution may be preheated with the separate heating element, pumped into the catheter, and dispensed into the user's body. The light may be turned on to supercharge the antimicrobial material while it may be dispensed or immediately after it may be dispensed and the catheter may be left in place until the treatment may be completed. The treatment may create a synergistic antimicrobial effect between an antimicrobial solution and a light of certain predetermined wavelengths. The resulting synergistic effect may be greater than the effect of an antimicrobial solution or the light acting alone.

In an exemplary embodiment depicted in FIG. 5, a retainer 140 may include a catheter 142 having a catheter tube 144, a mesh dispenser screen 146, and a fiber optic cable 148 having one or more light terminations. A heating element 152 may be external to the catheter tube 144, and may provide heated antimicrobial solution 154 through an input tube 156. A light source 158 may be connected through a fiber optic connection cable 160 to the fiber optic cable 148 with a fiber optic connection interface 162.

Figure 6:
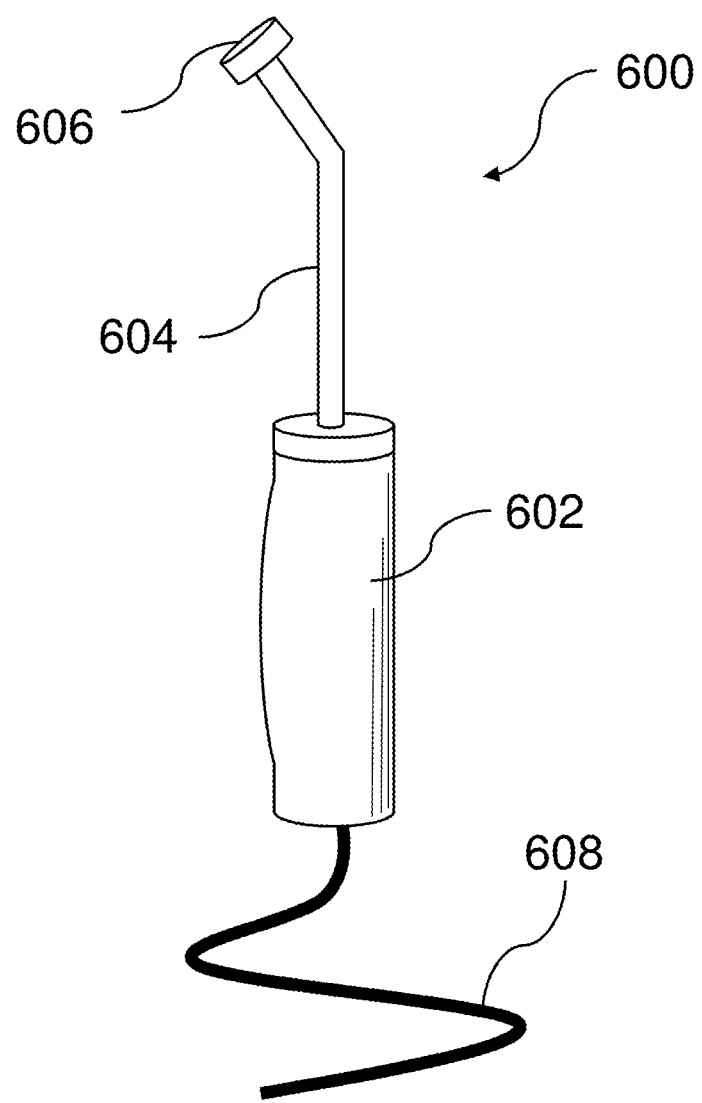
FIG. 6 is a diagram showing an exemplary embodiment of a hand-held light emitting device.

Now referring to exemplary FIG. 6, an exemplary embodiment of a hand-held light emitting device 600 may be provided. The hand-held light emitting device 600 may include a handle portion 602 rigidly connected to the first end of a neck 604. The second end of the neck 604 may be rigidly connected to a head portion 606 housing the light source outlet. In an exemplary embodiment, the light source may be situated in the handle portion 602 and the light may be guided through the neck 604 by optical element including, but not limited to, fiber optic and mirrors. It may be further appreciated that the neck 604 may be flexible and orientable. The light source may produce a light at a wavelength of about 360 nm to about 600 nm. In an exemplary embodiment, hand held light emitting device 600 may be used to irradiate an antimicrobial solution, thus creating a synergistic reaction with an antimicrobial effect greater than the light or the solution acting alone. In an exemplary embodiment, the hand-held light emitting device 600 may be powered by electric power. Power sources may include, but may not be limited to, batteries, rechargeable batteries, and grid power supply. The handle portion 602 may house any necessary elements required to provide the current and intensity required by the light source, such as electrical transformers and electronic components. In a further exemplary embodiment, the hand-held light emitting device 600 may be powered with batteries and may optionally require the power supply cable 608.

Figure 7A:
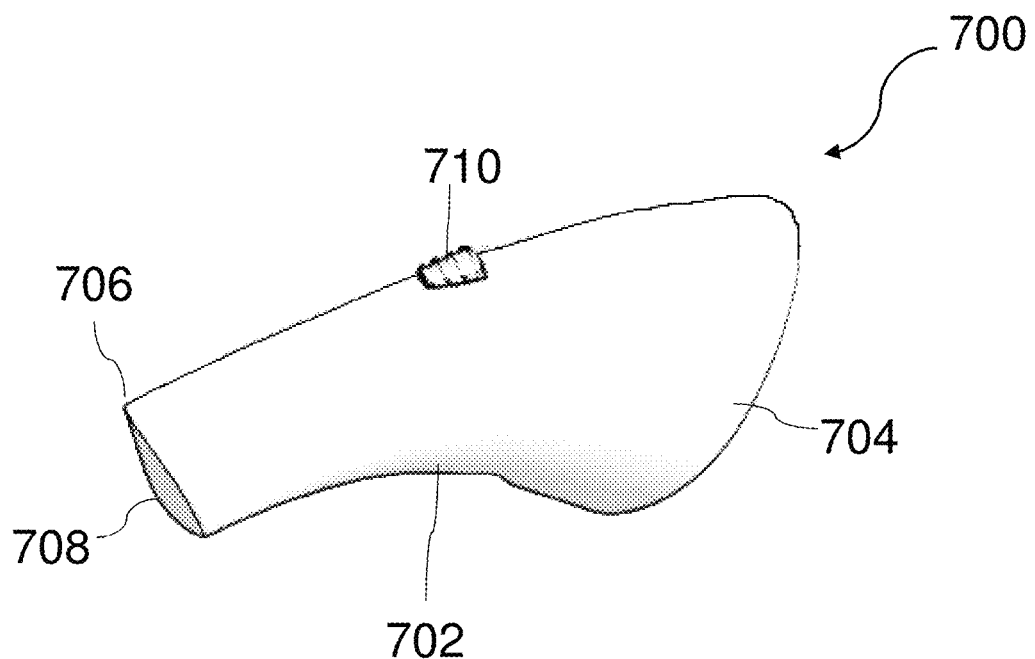
FIG. 7A is a diagram showing an exemplary embodiment of a portable light emitting device.
Figure 7B:
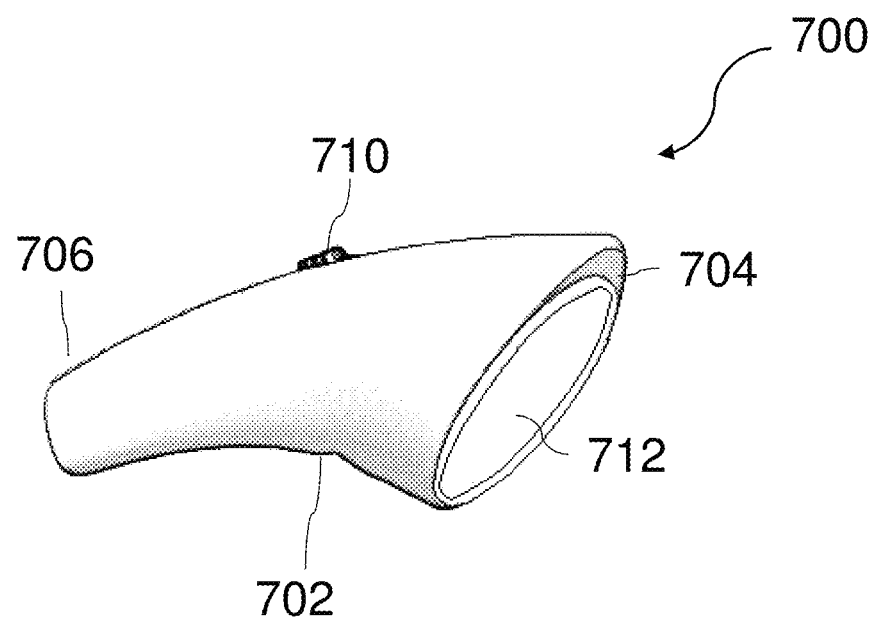
FIG. 7B is a diagram showing another exemplary embodiment of a portable light emitting device.

Now referring to exemplary FIGS. 7A and 7B, an exemplary embodiment of a portable light emitting device 700 may be provided. The portable light emitting device 700 may include a housing 702 having a conical shape with a wider end 704 and a narrower end 706. The housing 702 may be ergonomically shaped to fit comfortably in the palm of a hand. The narrower end 706 may include an output tip 708 for light from a light source housed within the device 700. It may be appreciated that the light source may be laser-based, LED-based or any desired type of light source, as would be understood by a person having ordinary skill in the art. Further, the light source may include a single source, multiple sources, or any combination of any desired sources, as may be understood by a person having ordinary skill in the art. The output tip 708 may be a circular opening having a diameter of 10 millimeters. It may be appreciated that the diameter of the output tip 708 may have any desired value. In an exemplary embodiment, the light source may be situated within the housing 702 proximate the wider end 704 and the light may be guided through the narrower end 706 by optical elements including, but not limited to, fiber optics and mirrors. The light source may produce light at a wavelength of about 385 nm to about 515 nm. In another exemplary embodiment, the light source may produce light at a wavelength of about 420 nm to about 480 nm. A power button or switch 710 may be disposed on an outer surface of the housing 702 to turn the device 700 on and off and further control a power level of the light source. The power level of the light source, for example, may be adjustable between a low, medium, and high level power setting. Any necessary elements needed to provide the current and intensity required by the light source, including, but not limited to, a power source (e.g., batteries), electrical transformers and electronic components may be housed proximate the wider end 704. The wider end 704 may be substantially or completely closed by a removable or hinged cover 712. In an exemplary embodiment, portable light emitting device 700 may be used to irradiate an antimicrobial solution, thus creating a synergistic reaction with an antimicrobial effect greater than the light or the solution acting alone. The output tip 708 may be held in direct contact against a surface with antimicrobial solution, or may alternatively be held at a distance that promotes full irradiation of the treatment area underneath. In an exemplary embodiment, the distance may not exceed 2 mm.

MRSA presents a significant health and economic hardship. Several new strains of MRSA exhibit antibiotic resistance to the current only antibiotics that are available to treat this infection. This patent describes a treatment that eliminates the MRSA bacterium and those of other nosocomial infection causing pathogens. MRSA is carried by 2 percent of the population and this percentage is increasing. The infection rate is expected to increase as more people become hosts to this bacterium and as more resistant strains evolve. MRSA is beginning to show up present in healthy people who have not been hospitalized. This type of MRSA is called community-associated MRSA, or CA-MRSA. According to the American Medical Association, the average age of people with MRSA in a hospital is 68. The average age of a person with CA-MRSA is 24. The treatment described in this patent offers a much-needed treatment option. An exemplary embodiment of the system, retainer and method of providing therapeutic treatment may decrease MRSA and other nosocomial infections by creating a synergistic antimicrobial effect between an antimicrobial solution and a light of certain predetermined wavelengths. The resulting synergistic effect may be greater than the effect of an antimicrobial solution or the light acting alone. In an exemplary embodiment, the system, retainer and method of providing therapeutic treatment generally referred to in FIGS. 1-6 may provide an improved method for the treatment of MRSA and other nosocomial infections involving the periodic application of an antimicrobial solution containing an effective amount of peroxide agents alone or in combination with one or more of a topical antibiotic, topical anesthetic, nicotinic acid, nicotinamide, antimicrobials, salicylic acid, sulfur, retinoids such as 6-[3-(1-adamantyl)-4-methoxy-phenyl] naphthalene-2-carboxylic acid, glycolic acid, tretinoin, borax, and additional chemicals useful in the method.

In other exemplary embodiments, the system, retainer and method of providing therapeutic treatment may utilize blue light, or another certain predetermined wavelength of light that may supercharge the solution, with an exposure from about a few seconds to a few minutes. In a further exemplary embodiment, the antimicrobial solution may be an $H_2O_2$ solution, such as a gel, with concentration of 0.3 mM or any concentration of solution that may be suitable as an antimicrobial agent. In an exemplary embodiment, hydrogen peroxide, if used alone may kill 30% of bacteria that may be exposed to it for 20 seconds. Similarly, a 20 second irradiation with light of the wavelength from 360 nm to 500 nm may kill 3% of bacteria that may be exposed to it. But then hydrogen peroxide in combination with light of 360 nm to 500 nm may exhibit a synergistic reaction that kills 96% of bacteria exposed to this combination for 20 seconds. This solution may work best at a temperature of about 57 degrees Celsius. It may be appreciated that other chemicals may have different preferred temperatures.

In an exemplary embodiment, and generally referring to FIGS. 1-6, topical solutions, including, but not limited to, hydrogen peroxide, carbamide peroxide, benzoyl peroxide and other chemicals deemed effective may be delivered in various organic vehicles or carriers. Exemplary embodiments of carriers may include a combination of ethyl alcohol and propylene glycol in which the active ingredient may present in the range of from about 0.001% to about 50% by volume of the carrier. The pH of the solution may be adjusted so that tissue sensitivity may be minimized while the effectiveness of the solution may not be hampered. The temperature of the solution may be adjusted to increase or optimize its effectiveness. In an exemplary embodiment, systemic antimicrobial agents may be used to increase the effectiveness of the treatment. The solution may be exposed to light in a wavelength of 360 nm to 600 nm or any other wavelength that proves effective for a certain time that may range from 1 second to 1 minute.

In an additional exemplary embodiment, topical solutions of peroxide compounds may include hydrogen peroxide and/or carbamide peroxide and/or benzoyl peroxide in various organic carriers in concentrations that may range from about 0.001% to about 50% by volume of the carrier.

In an exemplary embodiment, the antimicrobial solution may be incorporated into various vehicles or carriers including solutions, lotions, creams, gels, mists, pastes and ointments along with one or more of the following ingredients: nicotinic acid or nicotinamide that may be present in concentrations from about 0.001% to 30% by volume of the carrier.

In an exemplary embodiment, the antimicrobial solution may include erythromycin base in concentrations that may present from about 0.001% to about 30% by volume of the carrier.

In another exemplary embodiment, the antimicrobial solution may contain clindamycin phosphate methyl 7-chloro-6,7,8-trideoxy-6-(1-5 methyl-trans-4-propyl-L-2-pyrrolidinecarboxamido)-1-thio-L-threo-α-D-galacto-octop yrano side 2-(dihydrogen phosphate) with a concentration from about 0.001 to 30% by volume of carrier.

In another exemplary embodiment, the antimicrobial solution may contain tetracycline hydrochloride in concentrations of from 0.001 to 30% by volume of the carrier; retinoids such as 6-[3-(1-adamantyl)-4-methoxy-phenyl] naphthalene-2-carboxylic acid; It may be appreciated that the antimicrobial solution may contain any desired compounds deemed effective in treating acne vulgaris.

In still other exemplary embodiments, the antimicrobial solution carriers may include combinations of ethyl alcohol and propylene glycol, surface active agents such as lauryl ethers and lauryl esters, and other carriers effective for the desired purposes.

In other exemplary embodiments, the antimicrobial solution may include a light activated pigment that may fluoresce when exposed to the wavelength of light used in the treatment. This pigment may indicate to the user that the synergistic effect may be occurring.

Another exemplary embodiment may describe a method of decreasing prophylactically a person's normal flora of potential nosocomial infective microbes by administering a therapeutically effective amount of peroxide compounds and other therapeutic chemicals that together may form a solution that may be an effective antimicrobial compound for treatment. This solution, once applied, may be exposed to a wavelength of light, for example using embodiments described herein, that may create a synergistic antimicrobial effect that reduces or eliminates potential nosocomial infective bacteria. This synergistic antimicrobial effect may be greater than the solution's antimicrobial effect or the light's antimicrobial effect if they were used separately.

In one exemplary embodiment, an about 3% solution of hydrogen peroxide in a gel carrier may be prepared. Twice daily topical applications of this solution may be administered to an infected area on a patient suffering from acne vulgaris. After application, the solution may be exposed to light with a wavelength of about 360 nm to about 500 nm for 20 seconds (or some other amount of time) creating a synergistic effect that may be greater than 10 irradiations with the light or 10 applications the antimicrobial solution alone. The light may be applied by a LED device exposing the patient's entire infected area at one time. The solution may be then rinsed off with clean water. After treatment, the potential nosocomial infection causing bacterium count on the patient, may have measurably declined.

In another exemplary embodiment, a solution of containing chemical species including, but limited to, about 3% hydrogen peroxide, about 3% benzoyl peroxide, and salicylic acid may be combined in a cream form. This solution may be buffered to a pH of about 6. The cream may be applied to areas infected with MRSA once or multiple times on a patient daily. Once the cream is applied, it may be exposed to a 10-watt light source emitting at wavelengths from about 410 nm to about 500 nm thus creating a synergistic effect between the solution and the light causing a greater reduction in microbes than with the light or with the solution acting alone. The retainer may have a number of terminations having a diameter of about 15 mm. This particular size would enable the patient to target small areas. However, it may be appreciated that the diameter of the termination may have any desired value. The exposure time of the light may be about one minute. However, it may be appreciated that any desired duration of treatment may be selected. This exemplary embodiment may be used to maintain an area that once exhibited an active MRSA or other nosocomial infection.

In another exemplary embodiment, a solution containing chemical species including, but not limited to, about 15% carbamide peroxide, about 2.5% clindamycin phosphate (Methyl 7-chloro-6,7,8-trideoxy-6-(1-methyl-trans-4-prop yl-L-2-p yrrolidinec arbox amido)-1-thio-L-threo-α-D-galacto-octopyranoside 2-(dihydrogen phosphate)) and tretinoin may be combined in a gel-form carrier. The carrier gel may be heated to about 40 degrees Celsius. The warmed solution may help to open the patient's pores once it is applied to the infected area. This solution may be applied three times per day. The infected area may be exposed to a light of a wavelength from about 410 nm to about 500 nm by a number of light terminations that would expose an area with a diameter of about 30 centimeters. The infected area and solution may be exposed to this certain wavelength of light for about 30 seconds. The synergistic effect of the light and solution that may be warmed may be greater than the effect of the light or the solution acting individually.

EXAMPLES

Hereinafter, Examples will be described to explain the present invention in more detail, but the present invention is not limited thereto.

Example 1

Comparison of Antibacterial Activity of Synederm Light and Hydrogen Peroxide Combination Against Two Commercial Acne Products This example measures the antimicrobial efficacy of Synederm light and hydrogen peroxide on contaminated target surface areas. Testing procedures and study reports were generated by an independent laboratory, Antimicrobial Test Laboratories in Round Rock, Tex. The experiment was conducted pursuant to the American Society for Testing and Materials (ASTM) E1153, a quantitative test method designed to substantiate sanitizer claims for disinfectants on inanimate, non-porous, non-food contact surfaces. In particular, the study evaluated the efficacy of a Synederm light and hydrogen peroxide combination against two commercial acne products, Proactiv® Solution (benzoyl peroxide 2.5%) and Neutrogena® All-in-1 Acne Control (salicylic acid 1%). The commercial acne products were categorized based on their identified disinfecting ingredient.

The representative test microorganism used to conduct the study was *staphylococcus epidermidis* ("*S. epidermidis*"). *S. epidermidis* is a gram-positive, cocci-shaped, facultative anaerobe, living mainly on the skin's surface and mucosa. *S. epidermidis* is one of the most common organisms contributing to nosocomial infections due to the increase in medical usage of biomaterials. Specifically, *S. epidermidis* infections are associated with intravascular devices (prosthetic heart valves, shunts, etc.), prosthetic joints, catheters, and post-operative wounds and the urinary tract.

Tables 1 depicts the testing parameters used in preparation of testing microorganism *S. epidermidis*.

TABLE 1

| S. epidermidis | | | |
|---|---|---|---|
| Carrier size and Type | 1" × 3" Glass | Replicates | 1 |
| Test Substance (Vol.) | 0.030 mL | Culture Growth Time | 48 Hours |
| Culture Growth Media | Tryptic Soy Broth | Culture Supplement | None |
| Culture Dilution Media | None | Inoculum Volume | 0.005 mL |
| Target Concentration | 1 × 10$^6$ CFU/Carrier | Contact Temperature | 34 ± 1° C. |
| Contact Time | 10, 20, & 30 seconds for Test Substances and Synederm Light | Neutralizer (Vol.) | D/E Broth + 0.1% Catalase (20 ml) |

As used herein, "CFU" refers to "colony forming unit;" the term "Log Reduction" means Log(B/A), where B=the colony form unit (CFU) number of viable test microorganisms on the control carriers after the contact time and A=the colony form unit (CFU) number of viable test microorganisms on the test carriers after the contact time. All log numbers are base-10 logarithms. Specifically, $$\text{Log}_{10} \text{ Reduction} = \text{Log}\frac{B}{A}.$$

As an example, a Log Reduction of 4=99.9% of the bacteria killed and a Log Reduction of 6=99.999% of bacteria killed.

The ASTM E1153 protocol includes growing the test microorganism in a liquid culture medium. A series of hard, non-porous glass slides ("carriers") are inoculated with the representative test microorganisms, and subsequently dried in an incubator. ASTM E1153 utilizes non-antimicrobial agents as controls to establish baselines for microbial reductions. For this study, each inoculation area was kept to a 10 mm circle to match the output tip of the Synederm light source. Once completely dried, the inoculated test carriers were treated with the test substances and incubated for the predetermined contact time. The testing substances include: Synederm Light (385-515 nm), Synederm Light (420-480 nm), hydrogen peroxide (3%), benzoyl peroxide (2.5%), and salicylic acid (1%). Each Synederm light source was set to the high power setting for testing. Control carriers were treated with a buffered saline solution and allowed to sit for the predetermined contact time. At the conclusion of the contact time, treated carriers were transferred to vessels containing neutralizing media. Dilutions of the neutralized test substance were assayed for microbial survivors using appropriate growth media. To determine microbial reduction, the effect of the test substance is compared to the effect of the control substance.

Study results are reported as log reductions, indicating the differences of log CFU for inoculated, untreated control carriers and log CFU for inoculated, treated carriers according to the method provided herein. The percent reduction is determined by evaluating the number of microorganisms on the control carriers after the contact time with the number of viable microorganisms on the test carriers after contact time. Specifically, $$\text{Percent Reduction} = \frac{B - A}{B} \times 100.$$

ASTM International defines passing criteria to be a 3 $Log_{10}$ or 99.9% reduction in the treated test carriers when compared to the control carriers.

Tables 3-9 illustrate the results from Parts 1-3 of the study conducted in Example 1, measuring the antimicrobial efficacy of the various testing substances against *S. epidermidis*.

Parts 1 and 2 of Example 1 assessed the antimicrobial efficacy of each testing substance individually; the testing substances include: 3% hydrogen peroxide, 0.3% hydrogen peroxide, 1% salicylic acid, 2.5% benzoyl peroxide and Synederm light (420-480 nm). The stand-alone criteria measured the innate antimicrobial activity of each disinfecting testing substance. Table 3 depicts the effects of 3% hydrogen peroxide solution and 0.3% hydrogen peroxide solution at varying durations of exposure (10, 20 and 30 seconds). Table 4 depicts the effects of 1% salicylic acid and 2.5% benzoyl peroxide with a 30-second contact time. Table 5 depicts the effects of Synederm light (420-480 nm) with a 60-second contact time. *S. epidermidis* CFU/carrier concentration was most significantly reduced with a 3% hydrogen peroxide treated sample for 30-second contact time. However, none of the stand-alone samples satisfied the passing criteria set forth by ASTM International.

TABLE 2

Part 1

| Test Microorganism | Test Substance | Contact Time | Replicate | CFU/Carrier | Percent Reduction Compared to Control | $Log_{10}$ Reduction Compared to Control |
|---|---|---|---|---|---|---|
| S. epidermidis ATCC 12228 | Initial Numbers | | 1 | 1.4E+05 | N/A | |
| | 3% Hydrogen Peroxide | 10 Seconds | 1 | 7.50E+04 | 46.4% | 0.27 |
| | | 20 Seconds | 1 | 8.00E+04 | 42.9% | 0.24 |
| | | 30 Seconds | 1 | 6.30E+04 | 55% | 0.35 |
| | 0.3% Hydrogen Peroxide | 10 Seconds | 1 | 8.3E+04 | 40.7% | 0.23 |
| | | 20 Seconds | 1 | 7.50E+04 | 46.4% | 0.27 |
| | | 30 Seconds | 1 | 1.20E+05 | 14.3% | 0.07 |

TABLE 3

Part 1—Cont'd

| Test Microorganism | Test Substance | Contact Time | Replicate | CFU/Carrier | Percent Reduction Compared to Control | $Log_{10}$ Reduction Compared to Control |
|---|---|---|---|---|---|---|
| S. epidermidis ATCC 12228 | Initial Numbers | | 1 | 5.4E+05 | N/A | |
| | 1% Salicylic Acid | 30 seconds | 1 | 3.44E+05 | 36.3% | 0.20 |
| | 2.5% Benzoyl Peroxide | 30 Seconds | 1 | 4.80E+05 | 11.1% | 0.05 |

TABLE 4

Part 2

| Test Microorganism | Test Substance | Contact Time | Replicate | CFU/Carrier | Percent Reduction Compared to Control | $Log_{10}$ Reduction Compared to Control |
|---|---|---|---|---|---|---|
| S. epidermidis ATCC 12228 | Initial Numbers | | 1 | 8.10E+04 | N/A | |
| | Synederm Light (420-480 nm) | 60 seconds | 1 | 4.90E+04 | 39.5% | 0.22 |

Part 3 of Example 1 tested the antimicrobial efficacy of the various testing substances (0.3% hydrogen peroxide, 3.0% hydrogen peroxide, 2.5% benzoyl peroxide, 3.0% hydrogen peroxide+2.5% Benzoyl Peroxide, 1.0% salicylic acid and 1.0% salicylic acid+3.0% hydrogen peroxide) in combination with two different Synederm light sources. A first array of testing substances was treated with Synederm light at 420-480 nm, and a second array of testing substances was treated with Synederm light at 385-515 nm. Each array was evaluated at varying durations of exposure (10, 30, and 60 seconds). Tables 6-9 display the results of Part 3.

TABLE 5

Part 3

| Test Microorganism | Test Device | Test Substance | Contact Time (Synederm Light) | Replicate | CFU/ Carrier | Percent Reduction Compared to Control | Log$_{10}$ Reduction Compared to Control |
|---|---|---|---|---|---|---|---|
| S. epidermidis ATCC 12228 | Numbers Control | | | 1 | 2.97E+05 | N/A | |
| | Synederm Light (420-480 nm) | 0.3% Hydrogen Peroxide | 10 Seconds | 1 | 1.30E+05 | 56.2% | 0.36 |
| | | | 30 Seconds | 1 | 1.30E+05 | 56.3% | 0.36 |
| | | | 60 Seconds | 1 | 2.28E+04 | 92.3% | 1.11 |
| | | 3.0% Hydrogen Peroxide | 10 Seconds | 1 | 2.19E+04 | 92.6% | 1.13 |
| | | | 30 Seconds | 1 | 6.20E+03 | 97.9% | 1.68 |
| | | | 60 Seconds | 1 | <1.00E+01 | >99.997% | >4.55 |
| | | 2.5% Benzoyl Peroxide | 10 Seconds | 1 | 1.74E+05 | 41.2% | 0.23 |
| | | | 30 Seconds | 1 | 1.42E+05 | 52.2% | 0.32 |
| | | | 60 Seconds | 1 | 9.60E+04 | 67.6% | 0.49 |
| | | 3.0% Hydrogen Peroxide + 2.5% Benzoyl Peroxide | 10 Seconds | 1 | 3.10E+04 | 89.5% | 0.98 |
| | | | 30 Seconds | 1 | 8.10E+03 | 97.3% | 1.56 |
| | | | 60 Seconds | 1 | 1.11E+02 | 99.96% | 3.43 |

TABLE 6

Part 3—Cont'd

| Test Microorganism | Test Device | Test Substance | Contact Time (Synederm Light) | Replicate | CFU/ Carrier | Percent Reduction Compared to Control | Log$_{10}$ Reduction Compared to Control |
|---|---|---|---|---|---|---|---|
| S. epidermidis ATCC 12228 | Numbers Control | | | 1 | 5.40E+05 | N/A | |
| | Synederm Light (420-480 nm) | 1% Salicylic Acid | 10 Seconds | 1 | 3.75E+05 | 33.9% | 0.18 |
| | | | 30 Seconds | 1 | 1.99E+05 | 63.1% | 0.43 |
| | | | 60 Seconds | 1 | 3.48E+04 | 93.6% | 1.19 |
| | | 1% Salicylic Acid + 3% Hydrogen Peroxide | 10 Seconds | 1 | 1.70E+05 | 68.5% | 0.50 |
| | | | 30 Seconds | 1 | 1.01E+05 | 81.3% | 0.73 |
| | | | 60 Seconds | 1 | 5.90E+04 | 89.1% | 0.96 |

TABLE 7

Part 3—Cont'd

| Test Microorganism | Test Device | Test Substance | Contact Time (Synederm Light) | Replicate | CFU/ Carrier | Percent Reduction Compared to Control | Log$_{10}$ Reduction Compared to Control |
|---|---|---|---|---|---|---|---|
| S. epidermidis ATCC 12228 | Numbers Control | | | 1 | 2.97E+05 | N/A | |
| | Synederm Light (385-515 nm) | 0.3% Hydrogen Peroxide | 10 Seconds | 1 | 7.58E+4 | 74.4% | 0.59 |
| | | | 30 Seconds | 1 | 3.66E+04 | 87.7% | 0.91 |
| | | | 60 Seconds | 1 | 9.10E+03 | 96.9% | 1.51 |
| | | 3.0% Hydrogen Peroxide | 10 Seconds | 1 | 5.80E+04 | 80.4% | 0.71 |
| | | | 30 Seconds | 1 | 1.34E+03 | 99.5% | 2.34 |
| | | | 60 Seconds | 1 | <1.00E+01 | >99.997% | >4.55 |
| | | 2.5% Benzoyl Peroxide | 10 Seconds | 1 | 9.40E+04 | 68.3% | 0.50 |
| | | | 30 Seconds | 1 | 6.60E+01 | 99.98% | 3.65 |
| | | | 60 Seconds | 1 | <1.0E+01 | >99.997% | >4.55 |
| | | 3.0% | 10 Seconds | 1 | 5.44E+04 | 81.7% | 0.74 |

TABLE 7-continued

Part 3—Cont'd

| Test Microorganism | Test Device | Test Substance | Contact Time (Synederm Light) | Replicate | CFU/Carrier | Percent Reduction Compared to Control | $Log_{10}$ Reduction Compared to Control |
|---|---|---|---|---|---|---|---|
| | | Hydrogen Peroxide + 2.5% Benzoyl Peroxide | 30 Seconds | 1 | 2.62E+04 | 91.2% | 1.05 |
| | | | 60 Seconds | 1 | 7.00E+02 | 99.76% | 2.63 |

TABLE 8

Part 3—Cont'd

| Test Microorganism | Test Substance | Contact Time | Replicate | CFU/Carrier | Percent Reduction Compared to Control | $Log_{10}$ Reduction Compared to Control | $Log_{10}$ Reduction Compared to Control |
|---|---|---|---|---|---|---|---|
| S. epidermidis ATCC 12228 | Numbers Control | | 1 | 5.10E+05 | | N/A | |
| | Synederm Light (385-515 nm) | | 10 Seconds | 1 | 1.05E+05 | 79.4% | 0.69 |
| | 1% Salicylic Acid | 30 Seconds | 1 | 4.96E+04 | 90.3% | 1.01 |
| | | 60 Seconds | 1 | 4.82E+04 | 90.5% | 1.02 |
| | 1% Salicylic Acid + 3% Hydrogen Peroxide | 10 Seconds | 1 | 3.82E+04 | 92.5% | 1.13 |
| | | 30 Seconds | 1 | 2.17E+03 | 99.6% | 2.37 |
| | | 60 Seconds | 1 | 1.60E+03 | 99.7% | 2.50 |

The effects of the various testing substances in combination with Synederm light showed significant reduction on the concentration of S. epidermidis when varying the duration of exposure. Exposing S. epidermidis to 3% hydrogen peroxide +Synederm light (420-480nm) for 60 seconds, 3% hydrogen peroxide +Synederm light (385-515nm) for 60 seconds, and 2.5% benzoyl peroxide +Synederm light (385-515nm) for 60 seconds resulted in the most significant reduction of microorganism concentration. Each of the aforementioned testing parameters also satisfied the ASTM International passing criteria percentage reduction.

Example 2

Virucidal Activity Evaluation of Synederm Light and Hydrogen Peroxide Combination Against Herpes Simplex Virus 1

This example measures the virucidal efficacy of Synederm light and hydrogen peroxide on target surface areas contaminated with herpes simplex virus 1. Testing procedures and study reports were generated by an independent laboratory, Antimicrobial Test Laboratories in Round Rock, Tex. The experiment was conducted pursuant to AOAC Official Method 961.02, a semi-quantitative method for evaluating the efficacy of liquid disinfectants on hard, non-porous surfaces. In particular, the study evaluated the efficacy of Synederm light (385-515 nm) coupled with 3% hydrogen peroxide solution.

The test microorganism selected for this study was herpes simplex virus 1 ("HSV-1"). HSV-1 is an enveloped, double-stranded DNA virus commonly known as a "cold sore". HSV-1 is usually acquired through direct contact with infected lesions, sores, and/or oral secretions.

Table 12 depicts the testing parameters used in preparation of testing microorganism herpes simplex virus 1.

TABLE 9

| Herpes Simplex Virus 1 (HSV-1), ATCC VR-260 | | | |
|---|---|---|---|
| Carrier size and Type | 1" × 3" Glass | Replicates | 1 |
| Contact Distance | ~2 mm | Harvest Media (Vol.) | 0.1% Catalase EMEM (1.0 ml) |
| Viral Inoculum Volume | 0.005 ml | Carrier Inoculation Area | 8 mm Diameter |
| Carrier Dry Time | 5 Minutes | Carrier Dry Conditions | Ambient |
| Contact Time | 2 Minutes | Contact Conditions | 25.8° C., 43% RH |
| Host Cell Line | Vero (ATCC CCL-81) | Cell Passage Number | 188 |
| Assay Medium | 2% FBS EMEM | Soil Load | None |
| Incubation Period | 7 Days | Incubation Conditions | 37° C., 5% $CO_2$ |

Briefly, the AOAC Official Method 961.02 used herein included thawing stock virus previously propagated on African Green Monkey kidney cells, and preparing the virus to the appropriate log density per carrier. A series of hard, non-porous glass carriers were inoculated with 0.005 ml of virus suspension, the inoculum spread to a diameter of 8 mm on each carrier. Inoculated carriers were subsequently dried at room temperature in Petri dishes with lids ajar for 5-20 minutes, or until visibly dry. One dry carrier was harvested with 2 ml of sterile cell culture infection media to determine the initial numbers control. One dry carrier was treated with hydrogen peroxide for a duration of one minute. At the end of the contact time, the Synederm light was applied to the carrier at a distance not exceeding 2 mm. All harvests were followed by use of a sterile cell scraper to remove viral films from the surface of each carrier. Suspensions from harvested carriers (control and test) were serially diluted ten-fold in the appropriate test medium and plated in quadruplicate onto permissive host cell monolayers in multi-well trays. Host cell-virus assay plates were incubated at 37±2° C. in a 5% $CO_2$ humidified atmosphere for the duration of the incubation period.

Viral and cytotoxicity titers (TCID50/TCLD50 and TCCD50, respectively) were determined according to the method developed by Spearman-Karber:

$$-\text{Log}_{10} \text{ of } 1st \text{ Dilution} - \left(\frac{\text{sum of \% mortality at each dilution}}{100}\right) - .5$$

Percent reduction of the virus is determined according to the following formula:

$$\text{Percent Reduction} = 1 - \left(\frac{C}{B}\right) * 100,$$

where B=Log10 of virus control carrier and C=log10 of virus test carrier.

Table 13 illustrates the results of the study conducted in Example 2.

TABLE 10

| Test Microorganism | Treatment | Contact Time | $Log_{10}$ Infectious Units per Carrier | $Log_{10}$ Reduction Relative to Control | Percent Reduction Relative to Control |
| --- | --- | --- | --- | --- | --- |
| Herpes Simplex Virus 1 (Oral Herpes) ATCC VR-260 | Control | | 4.00 | N/A | |
| | Synederm Light coupled with 3% Hydrogen Peroxide | 2 Minutes | 2.00 | 2.00 | 99.00% |

The effect of the treatment (Synederm light coupled with 3% hydrogen peroxide) showed significant reduction of viral concentration from the testing carrier. In particular, exposing viable HSV-1 to the treatment within the limited contact time of 2 minutes achieved 99% inactivation.

The foregoing description and accompanying figures illustrate the principles, preferred exemplary embodiments and modes of operation of the invention. However, the invention should not be construed as being limited to the particular exemplary embodiments discussed above. Additional variations of the exemplary embodiments discussed above will be appreciated by those skilled in the art.

Therefore, the above-described exemplary embodiments should be regarded as illustrative rather than restrictive. Accordingly, it should be appreciated that variations to those exemplary embodiments can be made by those skilled in the art without departing from the scope of the invention as defined by the following claims.

What is claimed is:

1. A method of providing therapeutic treatment, comprising:
    coupling a retainer that retains an antimicrobial solution against tissue having a nosocomial infection, said antimicrobial solution comprising at least one of 3% hydrogen peroxide and 2.5% benzoyl peroxide;
    connecting at least one antimicrobial solution delivery element to the retainer for therapeutic treatment;
    providing at least one piece of tubing having a first end connected to an antimicrobial solution reservoir and a second end connected to the at least one antimicrobial solution delivery element;
    providing at least one fiber optic cable having a first end connected to a light source;
    connecting at least one light termination rigidly to the retainer for therapeutic treatment and to the second end of the fiber optic cable;
    applying the antimicrobial solution on a tissue to be treated;
    retaining the antimicrobial solution against the tissue to be treated;
    providing a predetermined wavelength of light;
    bringing the antimicrobial solution to a predetermined temperature;
    irradiating the antimicrobial solution; and
    exposing the antimicrobial solution to light of 385 nm to 515 nm for a duration of more than 60 seconds to 2 minutes.

2. The method of claim 1, wherein the nosocomial infection is caused by a pathogen selected from the group consisting of methicillin-resistant *Staphylococcus aureus* (MRSA), *Staphylococcus epidermis*, and Herpes Simplex Virus 1 (HSV-1).

3. The method of claim 1, wherein the light source includes at least one of a light emitting diode (LED) and a laser.

4. The method of claim 3, wherein:
    the retainer includes a container comprising a bowl having an open top and a base beneath the bowl,
    the tissue is immersed in the bowl,
    the fiber optic cable wraps up an inner surface of the bowl, and
    the fiber optic cable has a number of light terminations so that the antimicrobial solution is lighted with the predetermined wavelength of light from the optic cable in the bowl so as to substantially illuminate the tissue immersed in the bowl from all sides.

5. The method of claim 3, wherein the piece of tubing is a catheter tube that receives the antimicrobial solution at a first end and a mesh on the catheter tube near a second end opposite the first end, to dispense antimicrobial solution, wherein the at least one light termination is located on the fiber optic cable proximate the mesh.

6. The method of claim 3, wherein:
a number of light terminations on the fiber optic cable are connected rigidly to the retainer and to the second end of the fiber optic cable, the light terminations emitting light from the fiber optic cable into the antimicrobial solution,
the light terminations are positioned and of sufficient quantity so that there is at least one light termination adjacent to an area that is desired to be pathogen free, and
the retainer is a dental tray that retains the antimicrobial solution in a cavity on a side of the tray, wherein the fiber optic cable is retained within the tray, the tissue is a number of teeth of the user, each of the teeth having two opposite sides, and the tray is shaped to hold the lighted antimicrobial solution against tissue to be treated.

7. A method of providing therapeutic treatment, comprising:
coupling a retainer that retains an antimicrobial solution against tissue having a nosocomial infection, said antimicrobial solution comprising 3% hydrogen peroxide;
connecting at least one antimicrobial solution delivery element to the retainer for therapeutic treatment;
providing at least one piece of tubing having a first end connected to an antimicrobial solution reservoir and a second end connected to the at least one antimicrobial solution delivery element;
providing at least one fiber optic cable having a first end connected to a light source;
connecting at least one light termination rigidly to the retainer for therapeutic treatment and to the second end of the fiber optic cable;
applying the antimicrobial solution on a tissue to be treated;
retaining the antimicrobial solution against the tissue to be treated;
providing a predetermined wavelength of light;
bringing the antimicrobial solution to a predetermined temperature;
irradiating the antimicrobial solution; and
exposing the antimicrobial solution to light of 420 nm to 480 nm for a duration of more than 60 seconds.

8. The method of claim 7, wherein the nosocomial infection is caused by *Staphylococcus epidermis.*

9. The method of claim 7, wherein the light source includes at least one of a light emitting diode (LED) and a laser.

10. The method of claim 9, wherein:
the retainer includes a container comprising a bowl having an open top and a base beneath the bowl,
the tissue is immersed in the bowl,
the fiber optic cable wraps up an inner surface of the bowl, and
the fiber optic cable has a number of light terminations so that the antimicrobial solution is lighted with the predetermined wavelength of light from the optic cable in the bowl so as to substantially illuminate the tissue immersed in the bowl from all sides.

11. The method of claim 9, wherein the piece of tubing is a catheter tube that receives the antimicrobial solution at a first end and a mesh on the catheter tube near a second end opposite the first end, to dispense antimicrobial solution, wherein the at least one light termination is located on the fiber optic cable proximate the mesh.

12. The method of claim 9, wherein:
a number of light terminations on the fiber optic cable are connected rigidly to the retainer and to the second end of the fiber optic cable, the light terminations emitting light from the fiber optic cable into the antimicrobial solution,
the light terminations are positioned and of sufficient quantity so that there is at least one light termination adjacent to an area that is desired to be pathogen free, and
the retainer is a dental tray that retains the antimicrobial solution in a cavity on a side of the tray, wherein the fiber optic cable is retained within the tray, the tissue is a number of teeth of the user, each of the teeth having two opposite sides, and the tray is shaped to hold the lighted antimicrobial solution against tissue to be treated.

13. A method of treating a nosocomial infection on a target surface area, comprising:
coupling a retainer that retains an antimicrobial solution against the target surface area on which the nosocomial infection is present, said antimicrobial solution comprising a carrier and at least one peroxide agent in an amount of 0.001 to 50% per volume of the carrier,
connecting at least one antimicrobial solution delivery element to the retainer for therapeutic treatment;
providing at least one piece of tubing having a first end connected to an antimicrobial solution reservoir and a second end connected to the at least one antimicrobial solution delivery element;
providing at least one fiber optic cable having a first end connected to a light source;
connecting at least one light termination rigidly to the retainer for therapeutic treatment and to the second end of the fiber optic cable;
applying the antimicrobial solution onto the target surface area having the nosocomial infection;
retaining the antimicrobial solution against the target surface area;
providing a predetermined wavelength of light;
bringing the antimicrobial solution to a predetermined temperature;
irradiating the antimicrobial solution; and
exposing the antimicrobial solution to light of 385 nm to 515 nm for a duration of 1 second to 2 minutes.

14. The method of claim 13, wherein the target surface area is selected from the group consisting of: an intravascular device, a prosthetic joint, a catheter, and tissue.

15. The method of claim 13, wherein the nosocomial infection is caused by a pathogen selected from the group consisting of methicillin-resistant *Staphylococcus aureus* (MRSA), *Staphylococcus epidermis*, and Herpes Simplex Virus 1 (HSV-1).

16. The method of claim 13, wherein the at least one peroxide agent is at least one of hydrogen peroxide and benzoyl peroxide.

17. The method of claim 13, wherein the antimicrobial solution comprises at least one of 0.3% to 3% hydrogen peroxide per volume of the carrier and 2.5% to 3% benzoyl peroxide per volume of the carrier.

18. The method of claim 17, wherein the wavelength of light is from 420 nm to 480 nm or 410 nm to 500 nm.

19. The method of claim 17, wherein the duration of exposing the antimicrobial solution to the light is from 60 seconds to 2 minutes.

* * * * *